(12) United States Patent
Gough et al.

(10) Patent No.: US 11,583,640 B2
(45) Date of Patent: Feb. 21, 2023

(54) MEDICINE VAPORIZER APPARATUS AND METHODS OF USING THE SAME

(71) Applicant: Gough Industries, Inc., Crystal Lake, IL (US)

(72) Inventors: Steven Gough, Lakewood, IL (US); Joshua Gore, McHenry, IL (US)

(73) Assignee: Gough Industries, Inc., Crystal Lake, IL (US)

( * ) Notice: Subject to any disclaimer, the term of this patent is extended or adjusted under 35 U.S.C. 154(b) by 898 days.

(21) Appl. No.: 16/389,922

(22) Filed: Apr. 20, 2019

(65) Prior Publication Data

US 2019/0321569 A1   Oct. 24, 2019

Related U.S. Application Data

(60) Provisional application No. 62/660,735, filed on Apr. 20, 2018.

(51) Int. Cl.
*A61M 11/04* (2006.01)
*A61M 15/00* (2006.01)

(52) U.S. Cl.
CPC ...... *A61M 11/042* (2014.02); *A61M 15/0001* (2014.02); *A61M 2202/02* (2013.01);
(Continued)

(58) Field of Classification Search
CPC .............. A61M 16/108; A61M 11/042; A61M 15/0001; A61M 2202/02; A61M 2205/3368; A61M 2205/3334; A61M 2205/3358; A61M 2205/581; A61M 2205/583; A61M 2210/0625; A61M 16/0066; A61M 16/1095; A61M 2206/16; A61M 2016/102
See application file for complete search history.

(56) References Cited

U.S. PATENT DOCUMENTS 2,047,324 A * 7/1936 Inoue ................... A61M 11/042
128/203.26
2,199,724 A * 5/1940 Herbert ............. A61M 16/1075
128/204.17
(Continued)

FOREIGN PATENT DOCUMENTS

GB            526678 A  *  9/1940

*Primary Examiner* — Justine R Yu
*Assistant Examiner* — Matthew D Ziegler
(74) *Attorney, Agent, or Firm* — Scherrer Patent & Trademark Law, P.C.; Stephen T. Scherrer; Monique A. Morneault

(57) ABSTRACT

A medicine vaporizer apparatus comprises a base with an upwardly extending heating element disposed within a rigid tube. Air is drawn into the rigid tube through an aperture in the rigid tube below the heating element and directed over the heating element to then be drawn through a flexible tube and through a filter or screen comprising an amount of medicine. Heated air flows over the amount of medicine and vaporizes the same, wherein the medicine is thereafter drawn into the lungs of a patient pulling the air therethrough with his or her mouth. Thermal separation and cooling of various parts prevents accidental injury to users and provides an inert air path for the air therethrough. The apparatus further provides controlled incineration and/or vaporization of the medicine.

7 Claims, 4 Drawing Sheets

US 11,583,640 B2

Page 2

(52) U.S. Cl.
CPC .............. *A61M 2205/3368* (2013.01); *A61M 2210/0625* (2013.01)

(56) References Cited

U.S. PATENT DOCUMENTS

| | | |
|---|---|---|
| 4,653,494 A | 3/1987 | Ruderian |
| 5,511,539 A | 4/1996 | Lien |
| 6,772,756 B2 | 8/2004 | Shayan |
| 7,750,270 B2 | 7/2010 | Ji et al. |
| 8,739,786 B2 * | 6/2014 | Postma .................. A24F 40/46 128/203.26 |
| 8,781,306 B2 * | 7/2014 | Hatten .............. A61M 16/1075 392/386 |
| 8,910,630 B2 | 12/2014 | Todd |
| 9,149,586 B2 | 10/2015 | Shen et al. |
| 9,420,829 B2 | 8/2016 | Thorens et al. |
| 9,849,258 B2 * | 12/2017 | Klasek ................ A61M 16/024 |
| 10,512,282 B2 * | 12/2019 | Bowen .................... A24F 40/53 |
| 2003/0192532 A1 | 10/2003 | Hopkins |
| 2008/0271732 A1 * | 11/2008 | Weaver .............. A61M 15/025 128/200.14 |
| 2012/0219274 A1 | 8/2012 | Curran, Jr. et al. |
| 2014/0158129 A1 * | 6/2014 | Pratt, Jr. .............. A61M 11/042 128/203.26 |
| 2015/0125136 A1 | 5/2015 | Sanchez |
| 2016/0044960 A1 | 2/2016 | O'Connor |
| 2017/0055588 A1 | 3/2017 | Cameron |
| 2017/0197056 A1 * | 7/2017 | Van Schalkwyk ........................... A61M 16/0066 |
| 2017/0367408 A1 | 12/2017 | Pang |
| 2019/0307976 A1 * | 10/2019 | Grant ...................... A24D 3/17 |

* cited by examiner

MEDICINE VAPORIZER APPARATUS AND METHODS OF USING THE SAME

The present invention claims priority to U.S. Prov. Pat. App. No. 62/660,735 titled, "Medicine Vaporizer Apparatus and Methods of Using the Same," filed Apr. 20, 2018, which is incorporated herein by reference in its entirety.

TECHNICAL FIELD

The present invention relates to a medicine vaporizer apparatus. Specifically, the present invention comprises a base with an upwardly extending heating element disposed within a rigid tube. Air is drawn into the rigid tube through an aperture in the rigid tube below the heating element and directed over the heating element to then be drawn through a tube, namely a glass wand which holds an amount of medicine, then through a screen, and finally through a flexible tube. Therefore, heated air flows over the amount of medicine and vaporizes the same, wherein the medicine is thereafter drawn into the lungs of a user pulling the air therethrough with his or her mouth. Thermal separation and cooling of various parts prevents accidental injury to users and prevents or minimizes impurities in the air path for the air therethrough. The apparatus further provides controlled vaporization of the medicine.

BACKGROUND

Incinerators and/or vaporizers are generally known for introducing medicine into a patient's lungs. Indeed, there are many vaporizers on the market today, especially for purposes of introducing various drugs into a patient's bloodstream. Indeed, cigarettes, cigars, hookahs and other like "dry herb" incinerators may be considered crude incinerators intended to deliver a drug into a user's bloodstream.

Today, electronic vaporizers are used to deliver drugs into the lungs of users, whether for wellness, medicinal or recreational purposes. For example, vaporizers are often used to deliver medicine that may be used for aiding a user in their breathing, such as vaporizers that deliver albuterol or other like drugs to asthma patients. Indeed, certain herbs, such as damiana has been used for centuries to treat asthma and depression while peppermint is popular for its soothing flavor and is used to treat a wide variety of ailments.

Moreover, vaporizers are widely known and used as e-cigarettes to deliver nicotine and soothing flavors to a user. More recently, as more and more U.S. States have legalized cannabis for wellness and medicinal purposes and for recreational use, vaporizers are becoming more commonly used for delivering doses of cannabinoids to users thereof. Medicinally, cannabinoids are becoming popular to aid in many various ailments, due to its propensity to provide relief to an array of symptoms including pain, nausea, anxiety, and inflammation.

However, today's vaporizers often do not provide sufficient control for users. Indeed, oftentimes, medicine that is vaporized and components of the vaporizers may be heated to too high a temperature and may burn or scorch, causing unwanted byproducts and impurities within the delivery stream. Therefore, a need exists for an improved apparatus for vaporizing medicines. Specifically, a need exists for an improved apparatus for vaporizing medicines that provides better thermal control thereof. More specifically, a need exists for an improved apparatus for vaporizing medicines that prevents or minimizes unwanted by-products or impurities within a delivery stream.

Moreover, oftentimes in typical vaporizers, the thermal element that is used to vaporize medicines is not sufficiently thermally separated from other components thereof. Because the heating element must be sufficiently heated, the heat may transfer to other elements of the apparatus that may be touched by a user, which may lead to injury. Therefore, a need exists for an improved apparatus for vaporizing medicines that may have sufficient thermal separation between regions of the apparatus that may be touched by a user. Specifically, a need exists for an improved apparatus for vaporizing medicines that may aid in preventing or minimizing injuries to users thereof.

In addition, typical vaporizers often draw air that passes directly overheating elements and other components that may off-gas or otherwise decay under intense heat. Particles that may be introduced into a delivery stream may be toxic and harmful to a user thereof. Therefore, a need exists for an improved apparatus for vaporizing medicines utilizing inert materials. Specifically, a need exists for an improved apparatus for vaporizing medicines that prevents or minimizes harmful substances from entering the delivery stream that may be caused by the heating element and/or heating of surrounding materials. More specifically, a need exists for an improved apparatus for vaporizing medicines that provides a clean, inert air path for delivering medicine to a user's lungs.

Typical vaporizers utilize heating elements that may insufficiently controlled, and may consequently burn or overheat medicines. Indeed, certain medicines must typically be vaporized, and not combusted, but insufficient control of heating elements may lead to combustion thereof. Combustion causes many chemical reactions, and the creation of impurities that may detrimental, if not antithetical to the user attempting to obtain relief through the medicines. In addition, oftentimes medicines may act differently to a user based on their heating profiles during the vaporization process. For example, because medicines often contain complicated mixtures of chemicals, the temperature profile during vaporization may cause more or less of certain chemical compounds to be vaporized together, leading to undesirable effects. A need, therefore, exists for an improved apparatus for vaporizing medicines that provides precise control of the heating profile of vaporization of the medicines. Specifically, a need exists for an improved apparatus that minimizes or prevents combustion of medicines or other chemicals that can lead to undesirable impurities. Moreover, a need exists for an improved apparatus for vaporizing medicines that allows users to control specific temperature profiles to deliver desired combinations of chemicals after vaporization of the same.

SUMMARY OF THE INVENTION

The present invention relates to a medicine vaporizer apparatus. Specifically, the present invention comprises a base with an upwardly extending heating element disposed within a rigid tube. Air is drawn into the rigid tube through an aperture in the rigid tube below the heating element and directed over the heating element to then be drawn through a tube, namely a glass wand which holds an amount of medicine, then through a screen, and finally through a flexible tube. Therefore, heated air flows over the amount of medicine and vaporizes the same, wherein the medicine is thereafter drawn into the lungs of a user pulling the air therethrough with his or her mouth. Thermal separation and cooling of various parts prevents accidental injury to users and prevents or minimizes impurities in the air path for the air therethrough. The apparatus further provides controlled vaporization of the medicine.

To this end, in an embodiment of the present invention, an apparatus for vaporizing and/or incinerating medicine is provided. The apparatus comprises a base having a fan for directing air upwardly from the base; an outer shield extending from the base; an inner rigid tube extending from the base within the outer shield, wherein the fan directs airflow upwardly between the outer shield and the inner rigid tube; a heating element extending upwardly from the base within the inner rigid tube, the heating element terminating within the inner rigid tube and having a heated portion for heating air flowing thereover; an aperture within the inner rigid tube at a location below the heated portion of the heating element thereby directing airflow through the aperture from outside the inner rigid tube and over the heated portion of the heating element; and an extension tube connected to the inner rigid tube having a filter or screen for holding an amount of medicine and a mouthpiece on a terminal end thereof for a user to draw air therethrough.

In an embodiment, the outer shield is removable from the base.

In an embodiment, the base comprises an O-ring extending therearound for engaging the outer shield when the outer shield is disposed thereon.

In an embodiment, the base comprises openings having angled elements for directing airflow from the fan into the outer shield in a cyclonic manner.

In an embodiment, the apparatus further comprises: an air pump configured to direct air through the aperture into the inner rigid tube and thereafter into the extension tube.

In an embodiment, the inner rigid is removable from the base.

In an embodiment, the apparatus further comprises: at least one sensor for measuring a condition selected from the group consisting of temperature, pressure and airflow velocity.

In an alternate embodiment of the present invention, an apparatus for vaporizing medicine is provided. The apparatus comprises: a first tube through which air flows; a heating element extending and terminating within the tube and having a heated portion for heating air flowing thereover; an element holding an amount of at least one chemical thereon; and a first temperature sensor disposed adjacent the element holding the at least one chemical thereon.

In an embodiment, the element holding the at least one chemical thereon is disposed within an extension tube attached to the first tube.

In an embodiment, the apparatus further comprises: a second temperature sensor disposed proximal to the first temperature sensor.

In an embodiment, the first temperature sensor is configured to measure the temperature of heated air at the position of the first temperature sensor.

In an embodiment, the first temperature sensor is configured to measure the temperature of heated air at the position of the first temperature sensor and the second temperature sensor is configured to measure the temperature of heated air the position of the second temperature sensor.

In an embodiment, the apparatus further comprises: an ambient air pressure sensor configured to measure the ambient air pressure.

In an embodiment, the apparatus further comprises: an airflow velocity sensor outside of the first tube measuring the velocity of airflow into the first tube.

In an embodiment, the apparatus further comprises: an airflow velocity sensor within the extension tube measuring the velocity of airflow through the extension tube.

In an alternate embodiment of the present invention, a method of using an apparatus for vaporizing medicine is provided. The method comprises the steps of: providing an apparatus for vaporizing medicine comprising a first tube through which air flows, a heating element extending and terminating within the tube and having a heated portion for heating air flowing thereover, an element holding an amount of at least one chemical thereon, and a first temperature sensor disposed adjacent the element holding the at least one chemical thereon; and measuring the temperature of heated air at the position of the first temperature sensor.

In an embodiment, the method further comprises the steps of: providing a second temperature sensor disposed proximal to the first temperature sensor; and measuring the temperature of heated air at the position of the second temperature sensor.

In an embodiment, the method further comprises the steps of: providing an ambient air pressure sensor configured to measure the ambient air pressure; and measuring the ambient air pressure when using the apparatus to vaporize medicine.

In an embodiment, the method further comprises the steps of: providing an airflow velocity sensor within the first tube; and measuring the velocity of heated air through the first tube.

In an embodiment, the method further comprises the steps of: providing an extension tube extending from the first tube; providing an airflow velocity sensor within the extension tube; and measuring the velocity of airflow through the extension tube.

It is, therefore, an advantage and objective of the present invention to provide an improved apparatus for vaporizing medicines.

Specifically, it is an advantage and objective of the present invention to provide an improved apparatus for vaporizing medicines that provides better thermal control thereof.

More specifically, it is an advantage and objective of the present invention to provide an improved apparatus for vaporizing medicines that prevents or minimizes unwanted by-products or impurities within a delivery stream.

In addition, it is an advantage and objective of the present invention to provide an improved apparatus for vaporizing medicines that may have sufficient thermal separation between regions of the apparatus that may be touched by a user.

Specifically, it is an advantage and objective of the present invention to provide an improved apparatus for vaporizing medicines that may aid in preventing or minimizing injuries to users thereof.

Moreover, it is an advantage and objective of the present invention to provide an improved apparatus for vaporizing medicines utilizing materials that are maintained within their thermal limits to prevent or minimize impurities.

Further, it is an advantage and objective of the present invention to provide an improved apparatus for vaporizing medicines that prevents or minimizes harmful substances and impurities from entering the delivery stream that may be caused by the heating element and/or heating of surrounding materials.

Still further, it is an advantage and objective of the present invention to provide an improved apparatus for vaporizing medicines that provides a clean, inert air path for delivering medicine to a user's lungs.

Moreover, it is an advantage and objective of the present invention to provide an improved apparatus for vaporizing medicines that provides precise control of the heating profile of vaporization of the medicines.

Specifically, it is an advantage and objective of the present invention to provide an improved apparatus that minimizes or prevents combustion of medicines or other chemicals that can lead to undesirable chemicals and impurities.

More specifically, it is an advantage and objective of the present invention to provide an improved apparatus for vaporizing medicines that allows users to control specific temperature profiles to deliver desired combinations of chemicals after vaporization of the same.

Additional features and advantages of the present invention are described in, and will be apparent from, the detailed description of the presently preferred embodiments and from the drawings.

BRIEF DESCRIPTION OF THE DRAWINGS

The drawing figures depict one or more implementations in accord with the present concepts, by way of example only, not by way of limitations. In the figures, like reference numerals refer to the same or similar elements.

DETAILED DESCRIPTION OF THE PRESENTLY PREFERRED EMBODIMENTS

The present invention relates to a medicine vaporizer apparatus. Specifically, the present invention comprises a base with an upwardly extending heating element disposed within a rigid tube. Air is drawn into the rigid tube through an aperture in the rigid tube below the heating element and directed over the heating element to then be drawn through a tube, namely a glass wand which holds an amount of medicine, then through a screen, and finally through a flexible tube. Therefore, heated air flows over the amount of medicine and vaporizes the same, wherein the medicine is thereafter drawn into the lungs of a user pulling the air therethrough with his or her mouth. Thermal separation and cooling of various parts prevents accidental injury to users and prevents or minimizes impurities in the air path for the air therethrough. The apparatus further provides controlled vaporization of the medicine.

Figure 1:
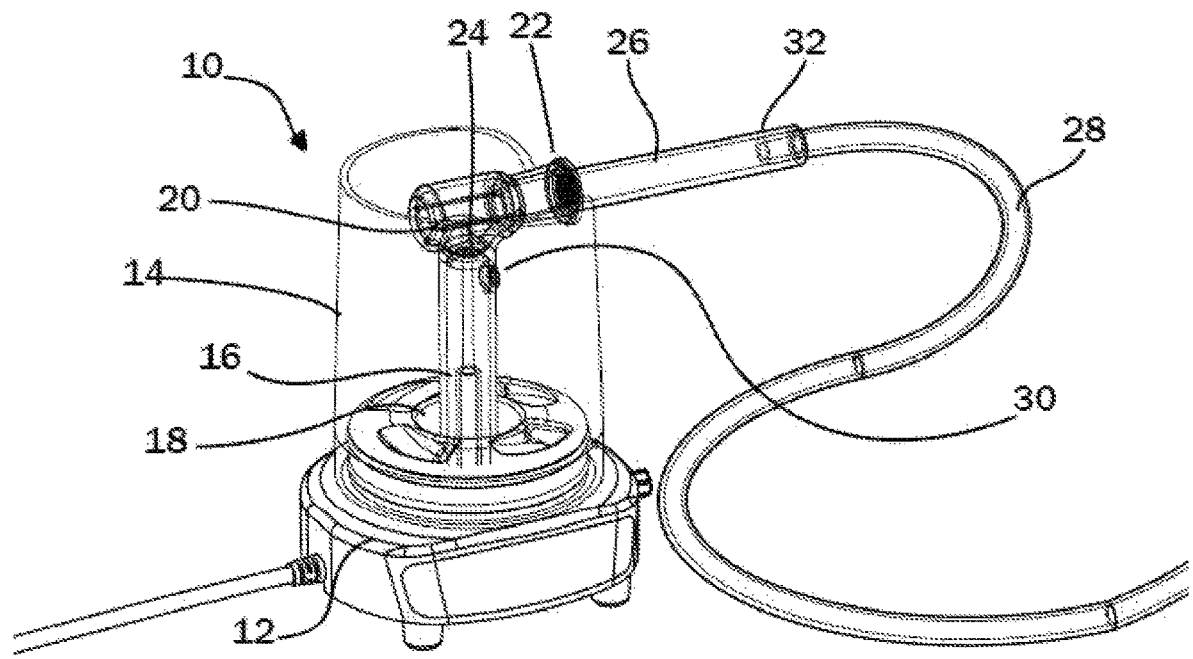
FIG. 1 illustrates a perspective view of a vaporizer apparatus in an embodiment of the present invention.
Figure 2:
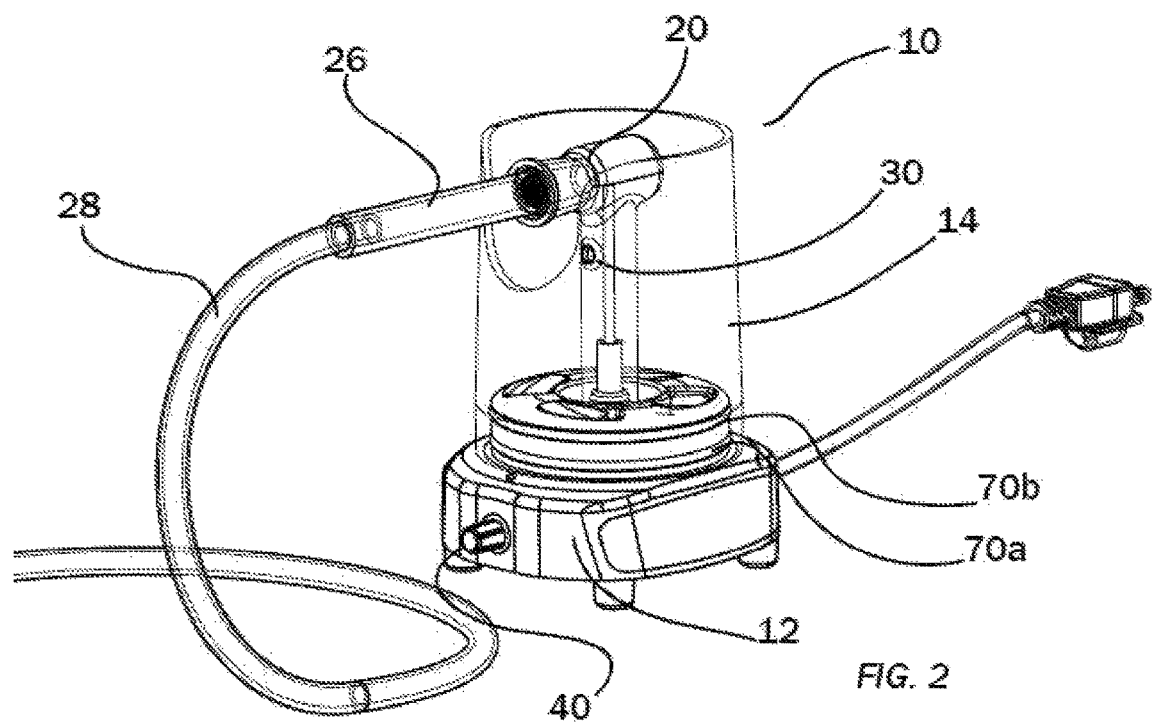
FIG. 2 illustrates a front view of a vaporizer apparatus in an embodiment of the present invention.

Now referring to the drawings, wherein like numerals refer to like parts, a vaporizer apparatus 10 is illustrated in FIGS. 1 and 2, and described in further detail below. In a preferred embodiment, the vaporizer apparatus 10 vaporizes medicine for inhalation by a user thereof, while shielding a user from heated components that may cause injury, and without burning or over-heating the medicine that would lessen the effectiveness thereof.

In an embodiment, the vaporizer apparatus 10 comprises a base 12 where, perched thereon and extending upwardly vertically from a top thereof is a roughly cylindrical shield 14. Disposed within the shield 14 may be a rigid tube 16 extending from an internal well 18 of the base 12, and the tube 16 may have a bend 20 at a top thereof and an opening 22 therein. The shield 14 and the rigid tube 16 may preferably be made of glass, although the shield 14 and the rigid tube 16 may be made from any material apparent to one of ordinary skill in the art that is generally inert within its thermal operating temperature range so that, when heated, does not off-gas or otherwise introduce impurities into an airstream. The tube 16 encapsulates a heating element 24 extending from a center of the well 18. An extension tube 26 extends from the opening 22, and a flexible hose 28 extends from the extension tube 26 to a mouthpiece (not shown) where a user may inhale medicine from the apparatus 10.

In use, the heating element 24 heats to a sufficient temperature to heat the air contained within the tube, and especially air that may be pulled through the tube 16 from a user inhaling the same through the flexible hose 28. When a user inhales air through the flexible hose 28, air may enter the tube 16 via an aperture 30 disposed below but roughly adjacent to the bend 20. Thus, fresh air from outside the tube 16 (specifically air that has not traversed over any electronic elements) travels through the aperture 30 and over the heating element 24, whereupon the fresh air is heated by the heating element 24, through the opening 22 and into the extension tube 26. The air then flows into the flexible hose 28, through the mouthpiece (not shown) and into the user's mouth and lungs. Medicine may be contained within the extension tube 26, which may be heated by the heated air flowing therethrough and vaporized by the heated air, and the heated air may thus traverse with the air into the user's lungs. Further, the user may also exhale at or toward the aperture 30 so that exhaled air, including unused medicine and other chemicals, may be directed toward the heating element 24 and back through the opening 22 into the extension tube 26. This may be useful for a number of reasons, such as to direct unused medicine back into the inhalation stream and/or for sensing chemicals that may be within the exhalation stream, as noted below with respect to one or more sensors that may be contained within the apparatus.

Figure 5:
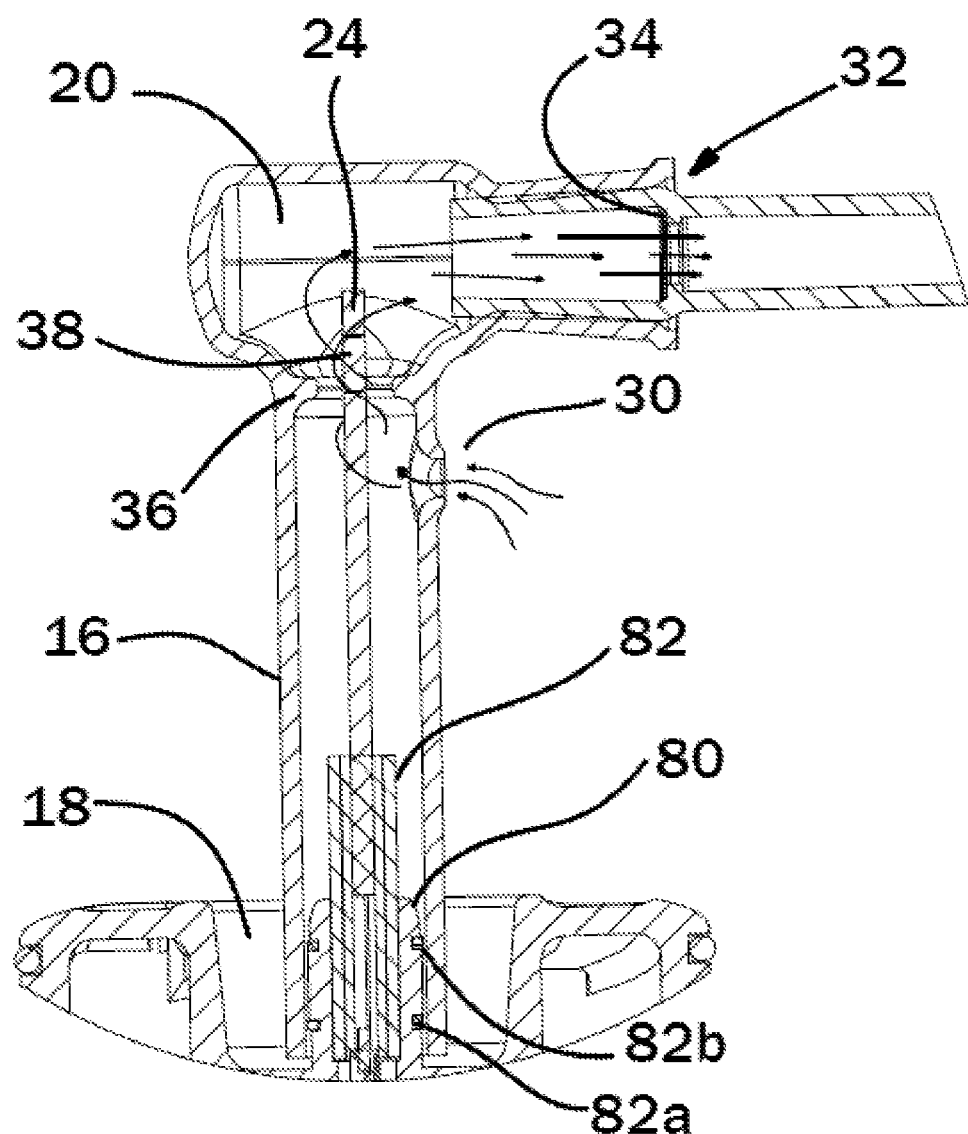
FIG. 5 illustrates a cross-sectional view of an inner tube and heating element of a vaporizer apparatus in an embodiment of the present invention.

The medicine may preferably be contained on or adjacent a filter or a screen 34 (as illustrated in FIG. 5) within the extension tube 26 so that the heated air may pass therethrough and vaporize the medicine. The medicine may be any medicine that may be vaporized and delivered to a user thereof. The screen or filter may be placed within extension tube 26 at roughly point or region 32, as illustrated in FIG. 1. Therefore, the heated air traversing through the filter or screen 34 may not be overheated as the medicine is placed a sufficient distance from the heating element 24.

FIG. 5 illustrates a close-up cross-sectional view of the rigid tube 16 in an embodiment thereof, illustrated airflow through the tube 16, over the medicine and through the filter or screen 34 at point or region 32 in the extension tube 26. Specifically, air may flow through aperture 30 and into tube 16, through a pinched neck portion 36, whereupon the decreased cross-sectional volume of the tube 16 at the pinched neck portion 36 may accelerate the airflow therethrough. The heated air may then traverse into the bend 20 and through the opening 22, over the medicine and ultimately through the filter or screen 34. The heating element 24 may have a specific heated region 38 so that the air flowing through the pinched neck portion 36 is heated at the heated region 38 as it accelerates therethrough. As the heated air travels through the extension tube 26, it vaporizes the medicine and carries the medicine to the user, whereupon the user inhales the medicine vaporized and carried by the heated air.

Preferably, the heating element 24 may be coated in ceramic or any other inert material to remain inert, especially when heated within the material's thermal operating range. Thus, the airflow therearound may remain clean and free of impurities, and the ceramic coating may prevent particles of, for example, metal, from off-gassing from the heating element, preventing or minimizing impurities within the airstream.

As illustrated in FIGS. 1 and 2, a control dial 40 may be disposed on the base for turning the apparatus 10 on and for controlling various aspects of the apparatus 10. Turning the dial 40 may cause the heating element 24 to heat as necessary. Preferably, turning the dial 40 to an activated position causes the heating element 24 to heat to a predefined and stable temperature. Alternatively, control dial 40 may allow a user to control the temperature of the heating element 24, as desired based on the medicine and the specific temperature needed to vaporize the medicine without damaging the same.

Figure 3:
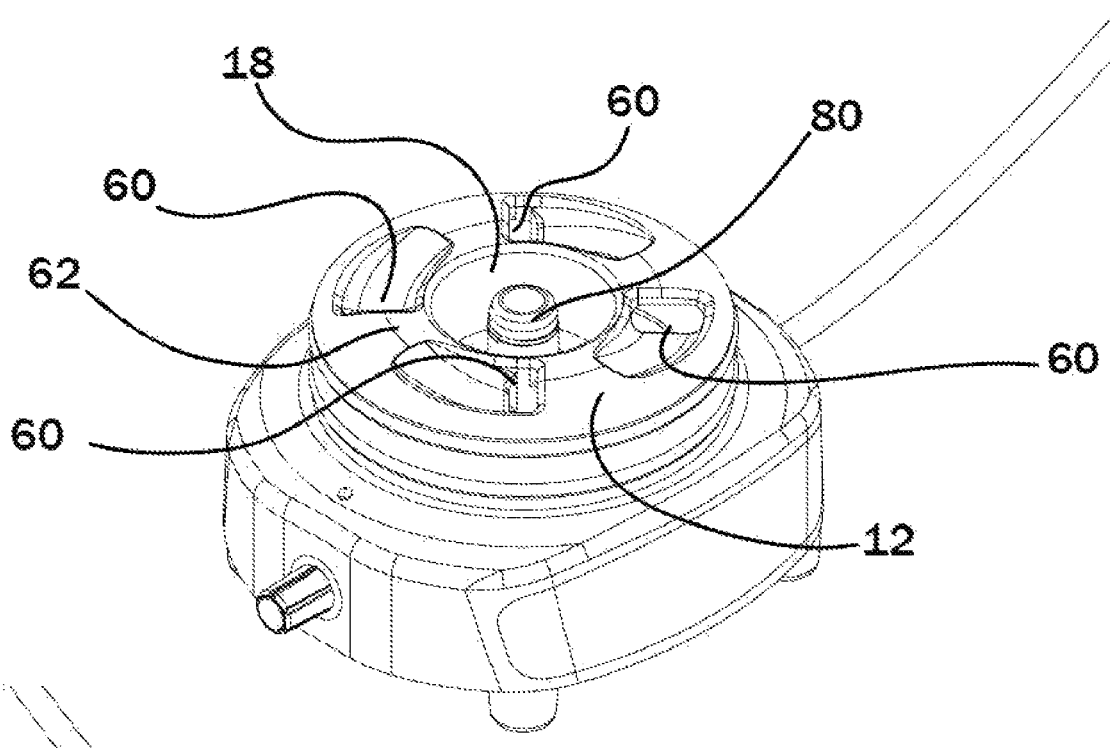
FIG. 3 illustrates a top view of a base for a vaporizer apparatus in an embodiment of the present invention.
Figure 4:
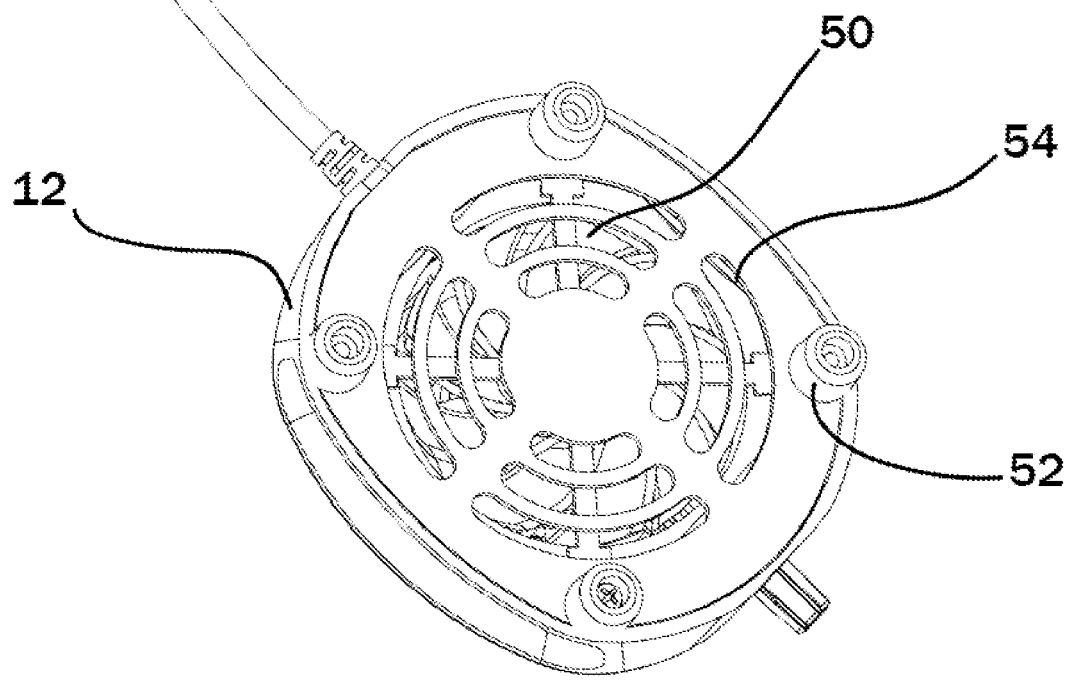
FIG. 4 illustrates a bottom view of a base for a vaporizer apparatus in an embodiment of the present invention.

The control dial 40 or any other controls may also activate a fan 50 (as illustrated in FIG. 4) contained within the base 12 which may pull air from the bottom of the base 12 through slits 54, as illustrated in FIG. 4. The bottom of the base 12 may include feet or legs 52 to ensure that there is sufficient clearance to pull air through the slits 54 via the fan 50 without interference. The fan 50 may pull the air from beneath the base 12, through the base 12, and out of angled vent holes 60 spaced around a top 62 of the base 12, as illustrated in FIG. 3. The angled vent holes 60 may be positioned circumferentially around the top of the base 12, and angled in the same direction, thus creating a cyclonic effect of air flowing within the shield 14 and out an open end of the shield 14 on a top end thereof. The relatively cool air movement out of the base 12 may thus flow around the rigid tube 16 cooling the same, and ensuring that the shield 14 also remains cool to the touch. Thus, a user may be protected from heated surfaces caused by the heating element 24. The cyclonic movement of air described herein may also aid in drawing fresh air into the aperture 30, as noted above. Specifically, the cyclonic air moves upwardly toward an outside of the space within the shield 14, drawing fresh air downwardly at or around the center of the space within the shield 14, thus, drawing fresh air down from above into the aperture 30.

Moreover, the heating element 24 may extend from a base 82 and, ultimately, a PCB board (not shown) that is disposed within the base 12, and further interconnected with the control dial 40 or any other controls. The heating element 24 may preferably be coated with ceramic, and may extend from the base 82 which may also preferably be made from ceramic, and the contact between the heating element 24 and the base 82 may be filled with a ceramic paste to provide minimal thermal connection between the heating element 24 and metallic components of the base of the apparatus 12, thereby ensuring that the base maintains a relatively cool temperature to prevent injury and to prevent or minimize impurities from entering the airstream, as described above. The heating element 24 may have minimal contacts with the PCB board to further the thermal separation thereof from other components of the apparatus 10.

The heating element 24 may be various shapes and/or configurations that may optimize the control of heated air and/or airflow velocity. The heating element 24 may have various holes, slits, bumps, grooves, bulges, or other like elements to provide different heat profiles to the air flowing therearound.

The PCB board may have the necessary electronic components to control both the heating of the heating element 24 and the fan 50 disposed therein. The apparatus 10 may be powered by any known means, such as via DC power through a plug, or via AC power via batteries, as apparent to one of ordinary skill in the art.

The shield 14 may be held onto the base 12 and may preferably be disposed thereon via O-rings 70a, 70b so that the shield 14 may be held thereon, but removable, as desired, such as for cleaning the same. Likewise, as illustrated in FIG. 5, rigid tube 16 may be held within well 18 on a base 80 within the well 18 via O-rings 82a, 82b so that the tube 16 may be removed, as needed. Of course, the shield 14 and tube 16 may be held thereon in any manner apparent to one of ordinary skill in the art, such as via adhesive, bolts, screws, or the like. The O-rings may be made from an elastomeric material that further provides thermal separation of the shield 14 and the rigid tube 16 from the base 12, so any heat generated and conducted through the base 12 may be thermally separated from the shield 14 and the rigid tube 16.

Therefore, air flowing through the apparatus from the fan 50 may ensure that the components of the apparatus 10 remain cool, thereby protecting a user from heated surfaces. Air may also flow through aperture 30 over the heating element 24 and the components thereof may remain inert, as described above, thereby keeping the air pure and free from contaminants.

Figure 6:
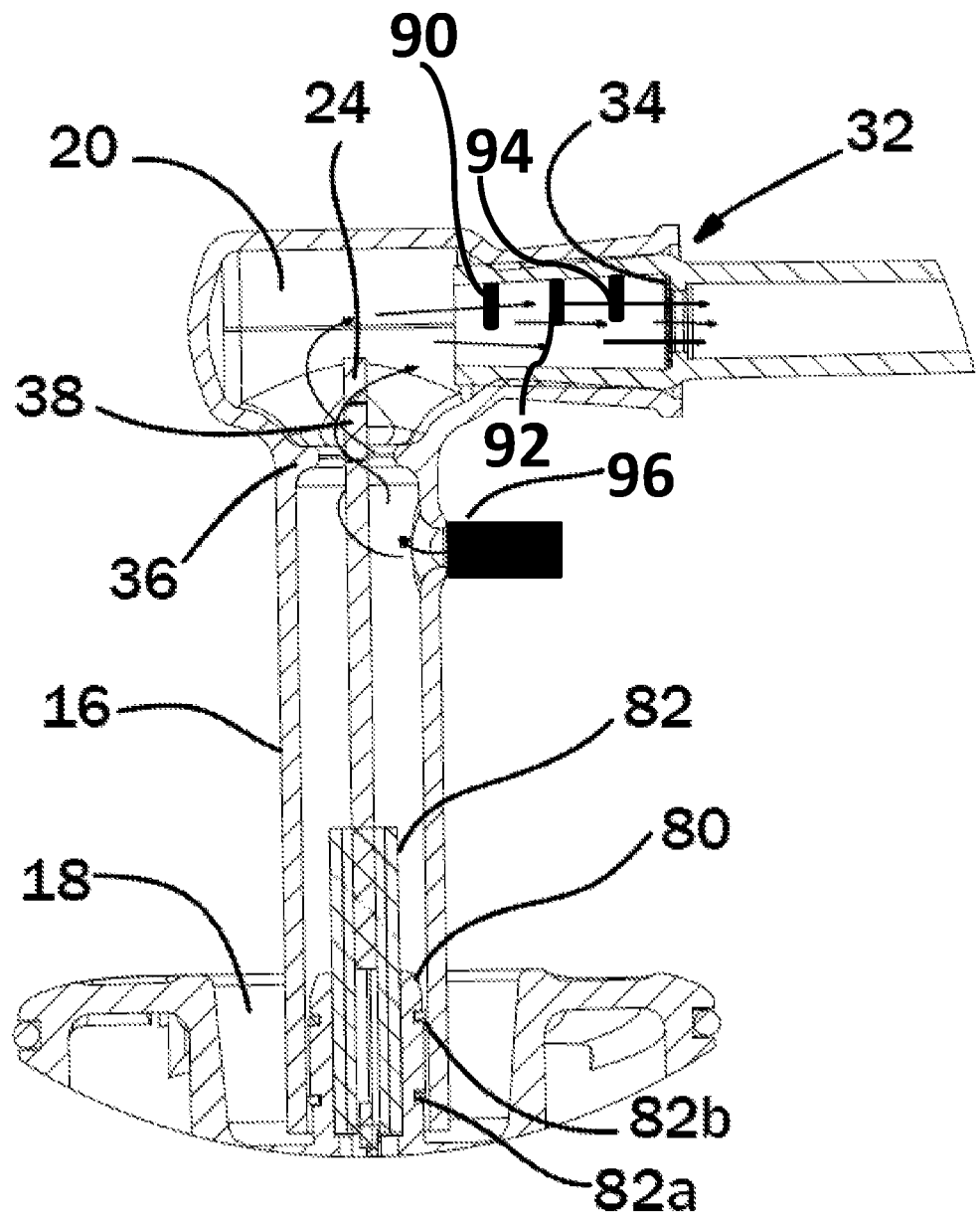
FIG. 6 illustrates a cross-sectional view of an inner tube and heating element of a vaporized apparatus with a plurality of sensors disposed therein in an embodiment of the present invention.

In an alternate embodiment of the present invention, FIG. 6 illustrates apparatus 10 comprising a plurality of sensors in various locations to provide certain information that may be useful to a user of the apparatus 10. Specifically, the apparatus 10 may include one or more temperature sensors, one or more airflow velocity sensors, one or more pressure sensors, and other like sensors for providing information concerning, mainly, the temperature and/or airflow velocity of the air flowing through the apparatus 10. As noted above, fresh air flows through aperture 30 and is heated via heating element 24 as it is drawn into extension tube 26 that may lead to the mouthpiece and delivered to the user. The various sensors may log readings of temperature, airflow velocity, pressure, carcinogens, or anything else desired by a user thereof to provide information concerning the delivery of the medicine to the user, such as after the medicine is delivered or during real-time delivery of the medicine.

For example, a plurality of temperature sensors may be contained at or near the screen 34 having the medicine thereon for vaporizing, as described above. The temperature sensors may provide information concerning the temperature of the air flowing therethrough, allowing the medicine to be vaporized in an optimal manner. For example, the medicine may vaporize at a narrow temperature range, wherein air at an undesired higher temperature may cause combustion of the medicine or other components, leading to impurities in the air stream when delivered to the user. Thus, the temperature sensors allow the user to determine whether the air flow therethrough is at the proper temperature.

Specifically, the apparatus 10 may have a front sensor 90, a mid-sensor 92, and a rear sensor 94, each of which may give specific temperature information that may allow a user to better obtain medicine. The front sensor 90 may be disposed a distance from the screen 34, toward a front opening of the extension tube 26; the rear sensor 94 may be positioned at or immediately adjacent the screen 34; and the mid-sensor 92 may be positioned at a location between the front sensor 90 and the rear sensor 94. Information concerning the temperature of the air flowing around temperature sensors 90, 92, 94 may provide information to the user about the extent of vaporization of the medicine on the screen 34 as the heated air flows therethrough.

As noted above, other sensors may include one or more airflow velocity sensors and/or pressure sensors, disposed in various locations, such as at or near the mouthpiece (not shown) that measures how fast the air flows therethrough. Thus, a user may be able to optimize the flow of heated air over the medicine contained on the screen 34, thereby aiding in optimizing the vaporization of the medicine thereon.

In addition, a sensor measuring volatile chemicals, combusted chemicals and/or carcinogens may also be contained within the apparatus 10 to provide information concerning the extent of and possible identification of impurities, such as incinerated materials, such as may occur if the temperature of the heated air is too high. Moreover, the amount or extent of materials that may be considered carcinogens may be measured to determine safety and efficacy of the medicines.

In another embodiment of the present invention, an ambient atmospheric pressure sensor may allow calibration of the apparatus depending on atmospheric pressure that may be influence the vaporization of medicine. For example, a user of the apparatus 10 at sea level is subject to a different atmospheric pressure than a user in the mountains, and these differences in atmospheric pressure may influence the vaporization of the medicine therein.

In an alternate embodiment of the present invention, an in-line air pump 96 may be utilized for pushing air through the apparatus 10, such as through the aperture 30, and may be utilized to ensure that the speed of heated air over the medicine is controlled. Again, the in-line air pump 96 may optimize the extent of vaporization of the medicine by ensuring that the heated air flows at the correct velocity. Thus, the temperature sensors and the in-line air pump 96 and/or airflow sensors or pressure sensors, may work together to ensure that the heated air has a desired temperature and air flow velocity profile to optimize the vaporization of the desired chemicals for delivery to the user. The in-line air pump 96 may also be utilized to automatically push heated air over medicine, where the heated air having vaporized medicine therein may be collected in a receptacle to be inhaled by a user when desired. Although the in-line air pump 96 is illustrated positioned over aperture 30 in FIG. 6, the air pump 96 may be in any position apparent to one of ordinary skill in the art to provide air flow velocity through the inner tube 20, as desired.

In use, the various sensors described herein may be used to optimize the vaporization of chemicals within the medicine contained on the screen 34. In other embodiments, the various sensors may allow chemicals within a complex mixture to be vaporized as desired to give a desired medicine profile, as different temperatures, pressures, and/or velocities may vaporize different amounts of various chemicals. Thus, different prescriptions of medicines may be prescribed based on differences in temperature, pressures and/or airflow velocity, which may be precisely controlled using the sensors disposed therein. The sensors may provide the optimized pharmacopedic recipe of medicine, offering the best delivery thereof to the user.

The various sensors may be connected to a control that may be utilized for analysis thereof. Specifically, the various sensors may be utilized to log reports that describe the various measurements during medicine inhalation. In other embodiments, the sensors may be utilized to provide real-time feedback to a user as the user is inhaling the vaporized medicine. A signal, such as an audible or visible signal may alert the user to optimized or non-optimized vaporization of medicine. For example, the various sensors may provide a user with real-time feedback that the vaporization is optimized or non-optimized by lighting an LED light, for example, indicating optimization of vaporization based on the temperature, pressure, and/or air flow velocity profile measured by the sensors.

In another embodiment, the control may utilize the sensed data, whether temperature, pressure, air flow velocity, impurity data, and other like data, to control the temperature of the heating element 24 and/or any air pumps that may push air through the inner tube 20, thereby determining via logic the optimum conditions by which medicine may be delivered to a user thereof. Thus, in a system of the present invention, the control may automatically determine the proper heating profile and/or airflow velocity profile to deliver the proper dose of medicine to the user thereof.

As noted above, the sensors may also be used to measure desired readings associated with exhaled air from the user after receiving the medicine. Because fresh air is drawn downwardly towards the aperture 30 from above the apparatus 10 due to the cyclonic air moving upwardly within the shield 14, a user may exhale into the apparatus 10 from above and the exhaled air may join the air drawn downwardly to re-enter the aperture 30. Thus, the sensors therein may be used to take readings of the exhaled air. For example, a chemical or impurity sensor within the apparatus 10 may thus be used to measure chemicals or impurities within user's exhalation stream. Of course, a separate unit may be provided that a user may exhale into for measuring desired characteristics of the exhalation stream, and the invention should not be limited as described herein.

It should be noted that various changes and modifications to the presently preferred embodiments described herein will be apparent to those skilled in the art. Such changes and modifications may be made without departing from the spirit and scope of the present invention and without diminishing its attendant advantages. Further, references throughout the specification to "the invention" are nonlimiting, and it should be noted that claim limitations presented herein are not meant to describe the invention as a whole. Moreover, the invention illustratively disclosed herein suitably may be practiced in the absence of any element which is not specifically disclosed herein.

We claim:

1. An apparatus for vaporizing medicine comprising:
a base having a fan for directing air upwardly from the base, the base having a top;
an outer shield extending from the top of the base and an opening at the top of the outer shield;
an inner rigid tube extending from the top of the base within the outer shield, the inner rigid tube comprising a side wall and a bottom, wherein the bottom of the inner rigid tube is sealed to the base to prevent air from entering the inner rigid tube from the bottom of the inner rigid tube;
openings in the top of the base configured to direct first airflow from the fan within the base upwardly between the outer shield and the inner rigid tube and through the opening in the top of the outer shield;
a heating element extending upwardly from the base within the inner rigid tube, the heating element terminating within the inner rigid tube and having a heated portion for heating air flowing thereover;

an aperture in the sidewall of the inner rigid tube at a location below the heated portion of the heating element thereby directing second airflow through the aperture from outside the inner rigid tube and over the heated portion of the heating element; and an extension tube connected to the inner rigid tube having an element configured to hold an amount of chemicals to be vaporized and a mouthpiece on a terminal end thereof for a user to draw air therethrough.

2. The apparatus of claim 1 wherein the outer shield is removable from the base.

3. The apparatus of claim 1 wherein the base comprises an O-ring extending therearound for engaging the outer shield when the outer shield is disposed thereon.

4. The apparatus of claim 1 wherein the openings in the top of the base have angled elements for directing airflow from the fan into the outer shield in a cyclonic manner.

5. The apparatus of claim 1 further comprising:
an air pump configured to direct the second airflow through the aperture into the inner rigid tube and thereafter into the extension tube.

6. The apparatus of claim 1 wherein the inner rigid tube is removable from the base.

7. The apparatus of claim 1 further comprising at least one sensor for measuring a condition selected from the group consisting of temperature, pressure and airflow velocity.

* * * * *